United States Patent [19]

Kohno et al.

[11] 4,082,457
[45] Apr. 4, 1978

[54] LEUKOCYTE DETECTOR

[75] Inventors: Hideki Kohno, Tokyo; Akihide Hashizume; Shinji Yamamoto, both of Hachioji, all of Japan

[73] Assignee: Hitachi, Ltd., Japan

[21] Appl. No.: 664,567

[22] Filed: Mar. 8, 1976

[30] Foreign Application Priority Data

Mar. 7, 1975 Japan .................................. 50-27113

[51] Int. Cl.² ............................................ G01N 33/16
[52] U.S. Cl. ......................................... 356/39; 356/184
[58] Field of Search .................................. 356/39–42, 356/184–186

[56] References Cited
U.S. PATENT DOCUMENTS 3,819,913  6/1974  Carter et al. ........................... 356/39
3,827,804  8/1974  Miller et al. ........................... 356/39

Primary Examiner—John K. Corbin
Assistant Examiner—Wm. H. Punter
Attorney, Agent, or Firm—Craig & Antonelli

[57] ABSTRACT

A leukocyte detector comprises a first and a second filter means adapted to select color components with different wave lengths, or green and blue color components, respectively, from the microscopic image of a stained blood smear, a first and a second opto-electric converter means for converting the transmitted light from said first and second filter means into corresponding electrical signals, a subtractor for subtracting the outputs from said first and second opto-electric converter means, and a comparator which compares the output of said subtractor with the predetermined threshold limit value.

1 Claim, 7 Drawing Figures

LEUKOCYTE DETECTOR

BACKGROUND OF THE INVENTION

1. Field of the Invention

This invention relates to a leukocyte detector, and more particularly to a device for detecting the leukocytes or white blood cells from a microscopic image of a stained blood smear.

2. Description of the Prior Art

Generally, the leukocyte count in the blood is far smaller than the erythrocyte count (the former is approximately 1/1000 of the latter), so that when one observes a hemogram under a microscope, he finds that most of the visual field is occupied by the erythrocytes. Thus, much time is usually taken for detecting the leukocytes when one tries to microscopically examine the leukocytes in a blood smear or to sort out the leukocytes automatically.

There is known in the art an automatic leukocyte sorting apparatus of the following system. In order to detect the leukocytes, first a part of the blood smear is scanned by a flying spot scanner to extract the blue color component and green color component from the transmitted light and these components are converted into corresponding electrical signals, which are then subjected to subtraction by a subtractor and the obtained differential signal is quantized and then guided to a leukocyte detector. A mask is set in this leukocyte detector, and if the pattern formed by said quantized signal is large enough to fill up said mask, it is determined that the leukocytes are present in that portion of the blood smear which was scanned. If no leukocyte is detected, the blood smear is moved by a stepping motor and similar scanning is performed over another portion of the smear.

Such a known leukocyte detecting system, however, has the drawbacks that the construction of the system is extremely complicated and much time is required for detecting the leukocytes as a time-consuming scanning means is used.

SUMMARY OF THE INVENTION

An object of the present invention is to provide a leukocyte detector which is capable of detecting leukocytes quickly.

Another object of the present invention is to provide a leukocyte detector which uses a simple mechanism.

In order to accomplish these objects, the present invention incorporates a novel device for discriminating the leukocytes from the erythrocytes by employing the peculiar spectral properties of the dyed leukocytes to allow quick detection of the leukocytes alone.

Generally, the blood smear on the slide is moved twodimensionally by the operation of a stepping motor or other means so that the small portions thereof will successively enter the visual field of the microscope; but according to the leukocyte detection system of the present invention, the quantity of light in each of the specified wave length areas in the entire visual field of the microscope, that is, in the entire microscopic image, is detected and converted into electrical signals by respective opto-electric converter means, and such signals are guided into the operational processing means, and it is determined whether leukocytes are present in said microscropic image from the strength of the signals obtained as a result of the operational processing.

DESCRIPTION OF THE PREFERRED EMBODIMENTS

Now the principles of the present invention will be described in detail with reference to the known peculiar characteristics of both leukocytes and erythrocytes.

Blood specimens are usually dyed for the convenience of microscopic observation. The dye used for this purpose is usually of the type composed of eosine-yellow, methylene-blue and azur, and it is known that the erythrocytes are dyed to eosine-yellow while the luecocytes are dyed to methylene-blue. (See, for example, J. H. Wright: Journal of Morphol, Vol. 20, p. 263, 1910; and I. T. Young: IEEE Transactions on Biomedical Engineering, Vol. BME-19, No. 4, p. 292, July, 1972).

Figure 1:
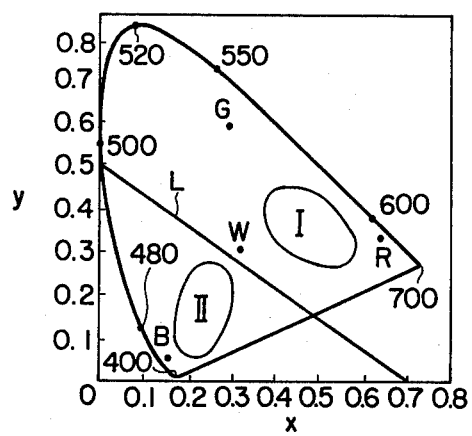
FIGS. 1 and 2 are graphic representations of the principles of the present invention.

If the above-said dye is used, the color of the erythrocytes becomes orangish-red while the color of the leukocyte nucleus becomes dark-bluish violet. So, if the distribution of the erythrocytes and leukocytes is represented to a known CIE chromaticity diagram according to the color features of both erythrocytes and leukocyte nucleus, there can be obtained a graphic manifestation such as shown in FIG. 1 since the erythrocytes have a color of yellow or red system while the leukocytes have a color of blue or purple system. (I. T. Young: Automatic Luekocyte Recognition, June, 1969, MIT Ph. Thesis).

In FIG. 1, the color zone indicated by I shows the range where the erythrocytes are present and the color zone indicated by II shows the range where the leukocytes exist. Also in the graph of FIG. 1, R, G and B represent the colors of red, green and blue, respectively. W represents white color or the location of the light source. As will be understood from the graph of FIG. 1, the zones indicated by I and II respectively can be separated by a straight line L, such zones can be determined by a discriminant function that can be obtained from the values on the x-axis and y-axis in the coordinates of FIG. 1 (that is, a straight line given by $\alpha x + \beta y = \gamma$). Thus, the zone I is involved in the area on the upper side of the line L in the graph where $\alpha x + \beta y > \gamma$, and the zone II is involved in the area on the lower side of said line L where $\alpha x + \beta y < \gamma$.

According to the detection system of the present invention, the presence of the leukocytes is determined from calculation of said discriminant function.

Figure 2:
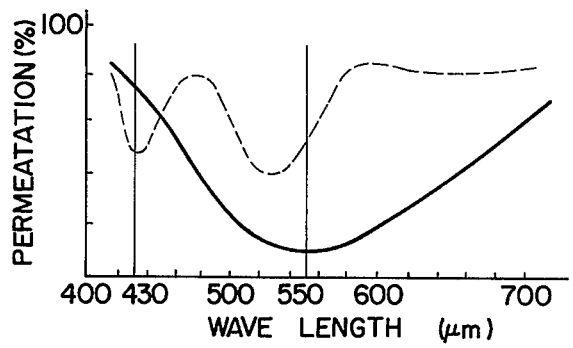

It is also known that the spectral properties of the erythroctyes and leukocytes, if analyzed based on the color difference of these two types of blood cells, can be diagrammed as shown by the graph of FIG. 2. (B H.

Sage: White Blood Cell Analyser, November, 1973, Laboratory Equipment Digest).

In the graph of FIG. 2, the abscissa represents wave length (μm) and ordinate represents permeation (%). The dotted line indicates the spectral properties of erythrocytes and the solid line expresses the spectral properites of leukocytes.

According to such spectral properties, it is noted that the leukocytes permeate substantially at the wave length of 430 μm and the erythrocytes alone can be observed. But at the wave length of 550 μm, the erythrocytes permeate at a relatively high rate and the leukocytes can be observed well. In other words, although permeation of the erythrocytes is substantially equal at the wave lengths of 430 μm and 550 μm, permeation of the leukocytes differs greatly at such wave lengths.

In the detection system of the present invention, the presence of said leukocytes is determined from a calculation of such a difference of permeation.

Figure 3:
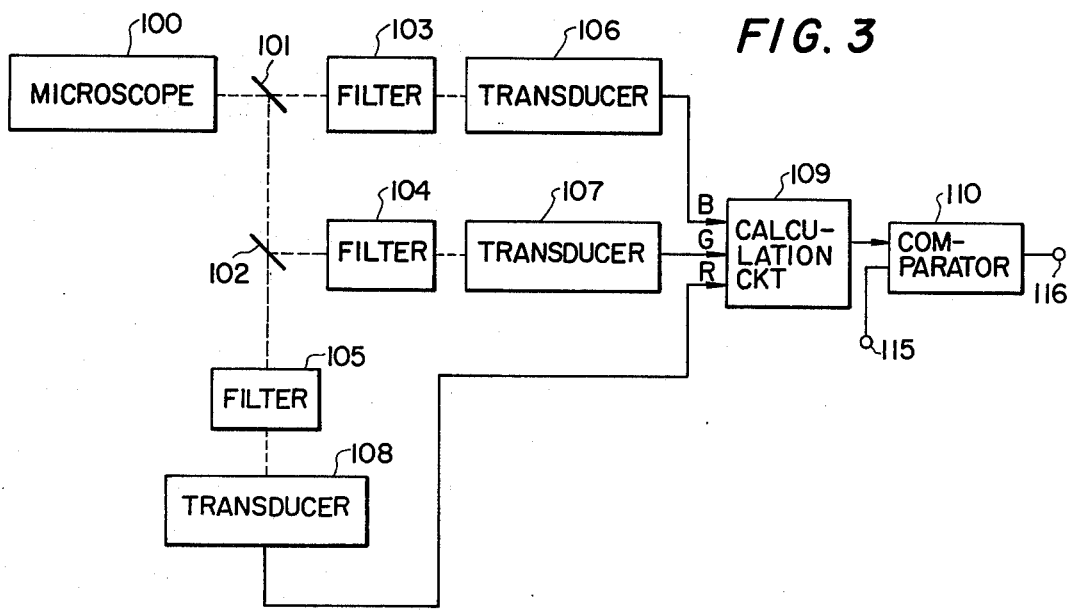
FIG. 3 is a block diagram showing the system in one embodiment of the present invention employing the principle illustrated in FIG. 1.

Referring now to FIG. 3, there is shown a block diagram of a system embodying the present invention. In the drawing, numeral 100 designates an optical microscope designed such that the microscopic light is trisected by means of halftransmitting mirrors 101, 102 optically connected to the ocular section of said microscope, and guided to the respective optical filters, or blue color filter 103, green color filter 104 and red color filter 105. The light beams which have transmitted said respective optical filters 103 – 105 are converted into corresponding electrical signals by means of opto-electric transducers such as photomultipliers 106, 107, 108, and these electrical signals are fed to a calculation circuit 109 as input signals. The above-mentioned discriminant function is obtained in said calculation circuit 109, and the result of its operational calculation is supplied to a comparator 110 as an input. This comparator 110 is also applied with a predetermined threshold limit value as another input.

Figure 4:
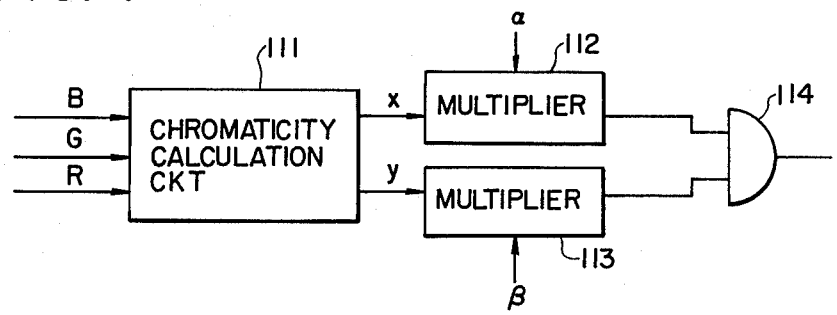
FIG. 4 is a block diagram showing some essential parts of the system of the present invention shown in FIG. 3.

The calculation circuit 109 has an arrangement such as shown in FIG. 4, that is, it comprises a chromaticity calculation circuit 111, a pair of multipliers 112 and 113, and an adder 114. The electrical signals B, G and R representing respectively the blue, green and red colors from the respective opto-electric transducers 106, 107 andd 108 are supplied to the chromaticity calculation circuit 111, where the values of $x$ and $y$ in the chromaticity diagram are calculated from the respective color components by a known method. The outputs $x$ and $y$ from said chromaticity calculation circuit 111 are impressed on the respective multipliers 112 and 113 as an input. These multipliers 112 and 113 are also applied with factors $\alpha$ and $\beta$ which are previously obtained from the straight line L shown in FIG. 1, and produce outputs $\alpha x$ and $\beta y$, respectively. These outputs are given to the adder 114. Consequently, this adder 114 produces an output equivalent to $\alpha x + \beta y$. Thus, comparator 110 is applied with the output of said adder 114 as an input and also applied with the factor $\gamma$ of said straight line L through a terminal 115 as another output. Therefore, if the output of the adder 114 is smaller than the factor $\gamma$, the blood specimen within the visual field of the microscope 100 will stay in the zone II in the graph of FIG. 1, and if the output of said adder 114 is greater than the factor $\gamma$, then the blood specimen within said visual field will stay in the zone I in the graph of FIG. 1. Thus, in FIG. 3, if an output is produced from the output terminal 116 of said comparator 110 when the output of the adder 114 is smaller than the factor $\gamma$, said output from said comparator 110 signifies existence of the leukocytes.

When no output is given through the output terminal 116, that is, when no leukocyte is present in the visual field presented by said microscope, the slide on which the blood specimen is stained is moved by a stepping motor or other means so as to present another visual field. The optical filters used in the system of the present invention may be neutral density filters.

Figure 5:
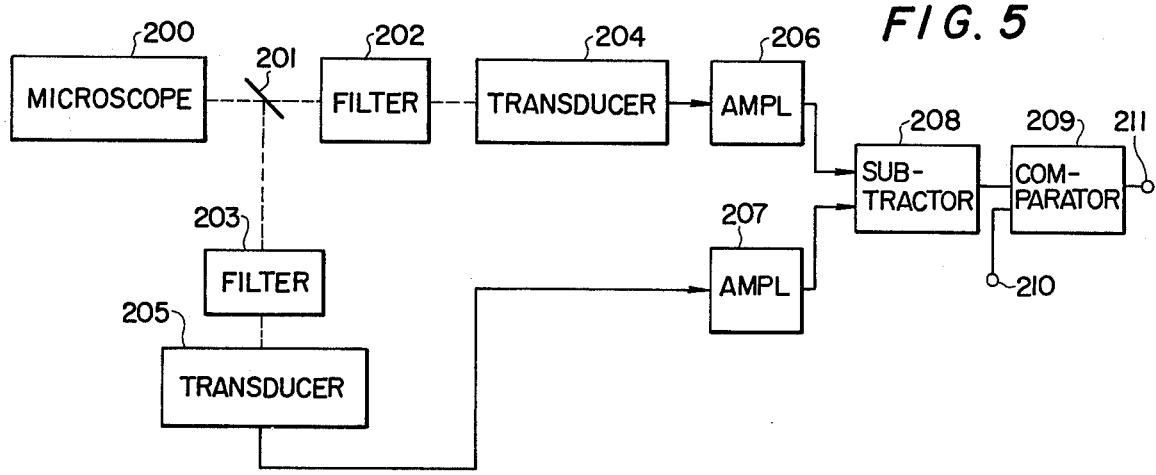
FIGS. 5 and 6 are block diagrams showing the systems according to other embodiments of the present invention adopting the principle of the invention illustrated in FIG. 2.

Referring to FIG. 5, there is shown a block diagram of a system according to another embodiment of the present invention, whereby the presence of leukocytes is detected by making use of the spectral properties graphically shown in FIG. 2.

In this system, the difference in light quantity resulting from the difference in permeation between erythrocytes and leukocytes at wave lengths of 430 μm and 550 μm shown in FIG. 2 is calculated, and if such a difference is greater than a prescribed threshold limit value C which is previously obtained from the graph of FIG. 2, it is determined that leukocytes are present.

According to this system, the light of the entire microscopic image is bisected by a half-transmitting mirror 201 optically connected to the ocular section of the optical microscope 200, and then guided to the respective opto-electric transducers 204 and 205 via respective optical filters 202 and 203. The output signals from said respective transducers are amplified by the respective amplifiers 206 and 207 and then supplied to a subtractor 208 where the difference between said both outputs is calculated and the resultant differential output is applied to a comparator 209 as an input. Said comparator 209 is also applied with a prescribed threshold limit value $C_1$ through a terminal 210 as another input. Let it here be assumed that a blue color filter (allowing transmission of light with wave lengths of from 420 to 440 μm) and a green color filter (allowing transmission of light with wave lengths of from 520 to 570 μm) are used as optical filters 202 and 203, respectively. There is a certain difference between the quantities of light of the green component and blue component allowing permeation of erythrocytes and leukocytes, respectively, as understood from the spectral properties graphically shown in FIG. 2, so that if the output of the amplifier 206 is subtracted from the output of the amplifier 207 in the subtractor 208, a greater difference is produced in the case of leukoctytes than in the case of erythrocytes. Therefore, if such a difference exceeds a certain set threshold limit value $C_1$ (which can be previously obtained from the graph of FIG. 2), it indicates that the leukocytes are present. In the comparator 209 shown in FIG. 5, the output of the subtractor 208 is compared with said threshold limit value $C_1$ and if the former is greater than the latter, an output is produced from said comparator 209 via its output terminal 211, signifying the presence of leukocytes.

The size of the optical microscopic image given to the opto-electric converters such as photomultipliers in the system of FIG. 5 is, for example, 2,000 μm² (200 μm × 10 μm. If the optical microscope used is one of 100 magnifications, it suffices to provide a 20 mm × 1 mm slit in front of each opto-electric converter). Usually, said size may be within the range of approximately 2,000 to 15,000 μm².

Figure 6:
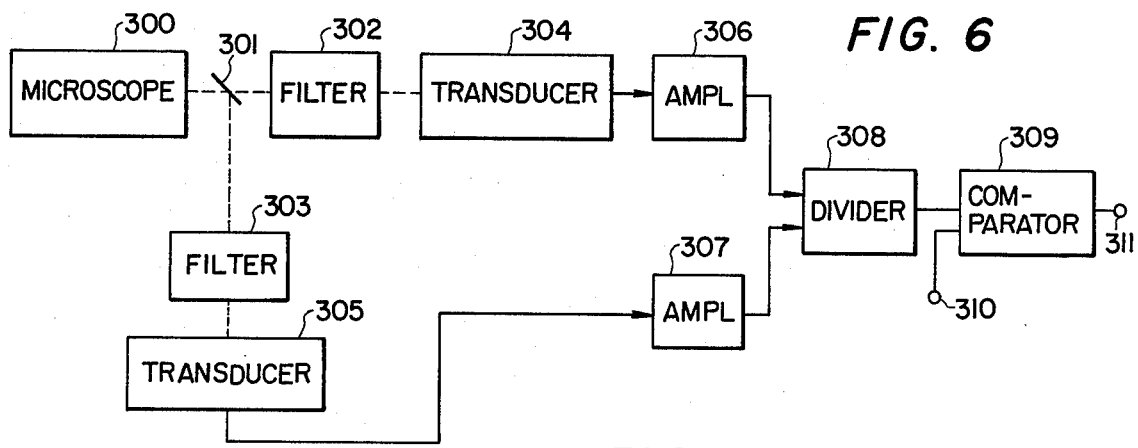

FIG. 6 is a block diagram showing a system according to still another embodiment of the present invention in which a divider is used in place of the subtractor in the embodiment shown in FIG. 5. The elements numbered from 300 to 307 in FIG. 6 are the same in construction as the counterparts numbered from 200 to 207 in FIG. 5. According to this system, the signal corresponding to the entire microscopic image opto-electrically converted through optical filters 302 and 303 (using a green color filter and a blue color filter) is divided by the divider 308 to calculate the difference between the light quantities of the green component and blue component that allow permeation of erythrocytes and leukocytes, respectively, and such a difference is fed as an input to a comparator 309 whcih is also applied with a predetermined threshold limit value $C_2$ via a terminal 310 as another input.

As noted from the graph of FIG. 2, the permeation rate of leukocytes in the range of wave lengths of blue and green components is far higher than that of erythrocytes, so that if the rate obtained within said wave length range is greater than the threshold limit value $C_2$ which is properly obtained from the graph of FIG. 2, it is learned that leukocytes are present. Thus, in the system of FIG. 6, presence of leukocytes is discerned by occurence of an output from the comparator 309 through its output terminal 311.

Although a blue color wave length range and a green color wave length range were used by way of exemplification in the embodiments of FIGS. 5 and 6, the green color wave length range may be substituted by a range where absorptivity of leukocyte nucleus is higher than that of erythrocyte.

Figure 7:
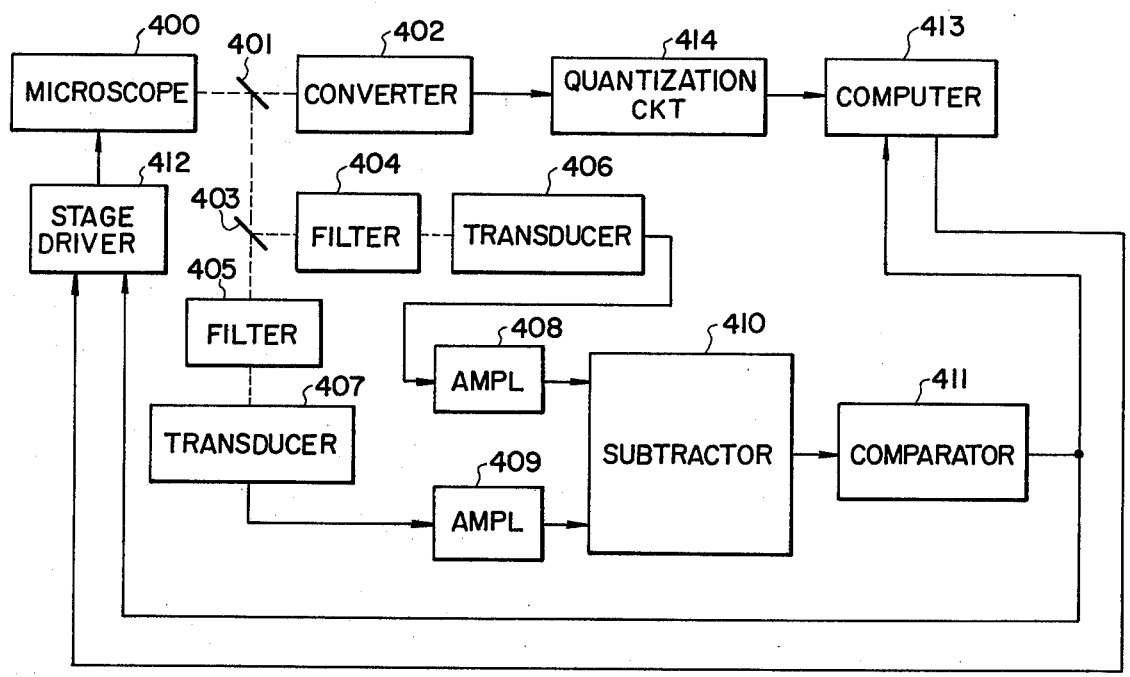
FIG. 7 is schematic block diagram of a leukocyte detector employing the system of the present invention shown in FIG. 3.

FIG. 7 shows a block diagram illustrating an example of adaptation of the embodiment of the present invention shown in FIG. 5 to an automatic leukocyte sorting apparatus. According to this system, the microscopic light is bisected by a half-transmitting mirror 401 optically connected to the ocular section of an optical microscope 400, with one portion of the bisected light being guided to an opto-electric converter means 402 designed for producing scanned electrical video signal such as generated by a TV camera, the remaining portion being guided to another half-transmitting mirror 403 whereby said portion of light is further bisected and, after undergoing spectral diffraction in the respective green and blue optical filters 404 and 405, passed into the respective opto-electric converters 406 and 407 for opto-electric conversion. The output signals from said opto-electric converters 406 and 407 are amplified by the respective amplifiers 408 and 409 and supplied to a subtractor 410 where the difference between said both output signals is calculated and further fed into a comparator 411 which determines whether leukocytes are present or not in the visual field of the microscope.

There is also provided a stage driver 412 for the optical microscope, which is actuated upon receiving an instruction from a computer 413 to start movement of the stage of the microscope, and when a leukocyte or leukocytes are detected in the visual field by the comparator 411, stage movement is stopped and at the same time the computer 413 is informed of the detection of leukocytes. The output signal of said opto-electrical signal converter means 402 is quantized by an quantization circuit 414 while continuously supplying the microscopic image to the computer 413, thereby to accomplish sorting of the leukocytes. Although only one opto-electrical signal converter means is used in this embodiment, plural units of such means may be provided so that each of them will make opto-electrical conversion of a picture in a particular wave length range.

As described above, there is provided according to the present invention a system which is capable of quickly determining whether leukocytes are present or not in the microscopic visual field on a microscopically observed blood smear, with a very simple mechanism.

What is claimed is:

1. A leukocyte detector comprising:

first means for resolving the entire microscopic image of a stained blood smear, each portion of said image being simultaneously observed, into respective spectral components with different wavelengths contained within at least the wavelength ranges 420 – 440 $\mu$m and 520 – 570 $\mu$m;

second means for measuring the light quantities of said respective spectral components;

third means for making a prescribed operational calculation by using as a variable each light quantity obtained from said second means; and fourth means for comparing the result of the calculation by said third means with a predetermined threshold limit value;

whereby the presence of leukocytes is indicated by the output from said fourth means; and wherein said third means comprises fifth means for calculating the abscissa and ordinate on a chromaticity diagram from the determined light quantities of the respective wave lengths, and sixth means for calculating the sum of the outputs from said fifth means, and wherein the output from said sixth means is compared with said threshold limit value.

* * * * *